| United States Patent [19] | [11] Patent Number: 4,777,136 |
|---|---|
| Young | [45] Date of Patent: Oct. 11, 1988 |

[54] MONOCLONAL ANTIBODY REACTIVE WITH *PSEUDOMONAS AERUGINOSA*

[75] Inventor: Lowell S. Young, San Francisco, Calif.

[73] Assignee: The Regents of the University of California, Berkeley, Calif.

[21] Appl. No.: 781,242

[22] Filed: Sep. 27, 1985

[51] Int. Cl.$^4$ ................... C12N 5/00; C07K 15/04
[52] U.S. Cl. ................... 435/240.27; 435/7; 435/68; 435/172.2; 530/387; 424/89; 436/548
[58] Field of Search .................. 424/89; 435/7, 172.1, 435/172.2, 875, 68, 240.27, 70; 436/548; 530/387, 388

[56] References Cited

U.S. PATENT DOCUMENTS 4,587,121  5/1986  Collins et al. ................... 424/87

FOREIGN PATENT DOCUMENTS 0101039  2/1984  European Pat. Off. .
0163493  12/1985  European Pat. Off. .
0174204  3/1986  European Pat. Off. .
0176365  4/1986  European Pat. Off. .
WO84/04458  11/1984  PCT Int'l Appl. .
WO85/01659  4/1985  PCT Int'l Appl. .

OTHER PUBLICATIONS

Structure of the Core Oligosaccharide from the Lipopolysaccharide of Pseudomonas aeruginosa PACIR and its Defective Mutants by Peters S. N. Rowe and P. M. Meadow, (1983).
Characterization of Polyagglutinating and Surface Antigens in *Pseudomonas Aeruginosa,* Journal of General Microbiology (1984).
Protection Against Infection with *Pseudomonas aeruginosa* by Passive Transfer of Monoclonal Antibodies to Lipopolysacchrides and Outer Membrane Proteins (J. of Infectious Diseases 1984).
"Functional Activity of Monoclonal Antibodies Againsg Lipopolysaccharide (LPS) Antigens of Gram Negative Bacilli," L. S. Young (UCLA Med. Ctr., L.A., CA), Clinical Research, 32;2, p. 518A (1984).
Sidberry et al., "Immunoenzymatic Analysis by Monoclonal Antibodies of Bacterial Lipopolysaccharides after Transfer to Nitrocellulose," *J. of Immunol. Meth.,* 76:299–305 (1985).
Sadoff et al., "Characterization of Mouse Monoclonal Antibodies Directed against *Pseudomonas aeruginosa* Lipopolysaccharides," *Antibiot. Chemother.,* 36:134–146, (Karger, Basel 1985).
Feingold et al., "Pseudomonas Infection," *Arch. Intern. Med.,* 116:326–28 (1965).
Abe et al., "Common Protective Antigen (OEP) of *Pseudomonas aeruginosa,*" *Jpn. J. Exp. Med.,* 45:355–359 (1975).
Zeigler et al., "Treatment of Gram–Negative Bacteremia and Shock with Human Antiserum to a Mutant *Escherichia coli,*" *N. Eng. J. Med.,* 307:1225–1230 (1982).
Hancock et al., "Monoclonal Antibodies Against Pseudomonas aeruginosa Outer Membrane Antigens: Isolation and Characterization," *Infect. Immun.,* 37:166–71 (1982).
Hiernaux et al., "Study of the Idiotypy of Lipopolysaccharide–Specific Polyclonal and Monoclonal Antibodies," *Eur. J. Immunol.,* 12:797–803 (1982).
Mackie et al., "Immune Response of the Mouse to Gram–Negative Bacterial Outer Membrane Extracts as Assessed with Monoclonal Antibodies," *J. Immunol.,* 129:829–32 (1982).
Young et al., "Monoclonal Antibody Directed Against the 'Core' Glycolipid of Enterobacterial Endotoxin," *Clin. Res.,* 30:522A (1982).

(List continued on next page.)

*Primary Examiner*—Margaret Moskowitz

[57] ABSTRACT

A hybridoma cell line identified by ATCC #HB8909, capable of producing monoclonal antibodies reactive with an antigenic determinant of lipopolysaccharide which is common to all strains of *Pseudomonas aeruginosa* and to *Pseudomonas maltophilia,* and is not reactive substantially with any antigenic determinant of other clinically important gram-negative bacteria is disclosed. Methods of producing the hybrid as well as diagnostic, prophylactic and therapeutic use of the monoclonal antibodies are also disclosed.

2 Claims, 1 Drawing Sheet

OTHER PUBLICATIONS

Pollack et al., "Enhanced Survival in *Pseudomonas aeruginosa* Septicemia Associated with High Levels of Circulating Antibody to *Escherichia coli* Endotoxin Care," *J. Clin. Invest.*, 72:1874-81 (1983).

Black et al., "Monoclonal Antibody (McAb) to Common Pathogenic Neisseria Antigen (H8Ag) Protects Against Meningococcemia (ME) in Mice," *Abstracts of the 1984 ICAAC*, 106.

Williams et al., "Panreactive Monoclonal Antibody (MCA) to Porin Protein F for *Pseudomonas aeruginosa* (PA)," *Abstracts of the 1984 ICAAC*, 106.

Kim et al., "Studies of the Protective Mechanism of Monoclonal Antibodies (Ab) Against *E. Coli* (EC)," *Abstracts of the 1984 ICAAC*, 160.

Mutharia et al., "Monoclonal Antibodies Specific for *Escherichia coli* J5 Lipopolysaccharide: Cross-Reaction with Other Gram-Negative Bacterial Species," *Infect. Immun.*, 45:631-36 (Sep. 1984).

Nelles et al., Mouse Monoclonal Antibodies Reactive with J5 Lipopolysaccharide Exhibit Extensive Serological Cross-Reactivity with a Variety of Gram-Negative Bacteria," *Infect. Immun.*, 46:677-81 (Dec. 1984).

Koval et al., "The Isolation and Characterization of Lipopolysaccharide-Defective Mutants of *Pseudomonas aeruginosa* PAC1," *J. Gen Micro.*, 98:387-398 (1977).

Kirkland et al., "An Immunoprotective Monoclonal Antibody to Lipopolysaccharide," *J. of Immunology*, 132:2590-2592 (1984).

Macario et al., "Antibacterial Monoclonal Antibodies and the Dawn of a New Era in the Control of Infection," *Surv. Synth. Path. Res.*, 3:119-130 (1984).

Young, L. S., "Gram-Negative Sepsis," *Principles and Practice of Infectious Disease*, pp. 452-475 (1985).

Teng et al., "Protection Against Gram-Negative Bacteremia and Endotoxemia with Human Monoclonal IgM Antibodies," *Proc. Nat. Acad. Sci. USA*, 82:1790-94 (Mar. 1985).

Gigliotti et al., "Failure of Monoclonal Antibodies to Core Glycolipid to Bind Intact Smooth Strains of *Escherichia coli*," *J. Infect. Dis.*, 151:1005-11 (Jun. 1985).

Peters et al., "Monoclonal Antibodies to Enterobacterial Common Antigen and to *Escherichia coli* Lipopolysaccharide Outer Core: Demonstration of an Antigenic Determinant Shared by Enterobacterial Common Antigen and *E. coli* K5 Capsular Polysaccharide," *Infect. Immun.*, 50:459-66 (Nov. 1985).

Dunn et al., "Efficacy of Type-Specific and Cross-Reactive Murine Monoclonal Antibodies Directed Against Endotoxin During Experimental Sepsis," *Surgery*, 98:283-90 (Aug. 1985).

Thornley et al., "Properties of Monoclonal Antibodies to the Genus-Specific Antigen of Chlamydia and Their Use for Antigen Detection by Reverse Passive Haemagglutination," *J. Gen. Microbiology*, 131:7-15 (1985).

Siadak and Lostrom, "Cell-Driven Viral Transformation," *J. Gen. Microbiology, 131:7-15 (1985)*.

Young, L. S., "Monoclonal Antibodies: Technology and Application to Gram-Negative Infections," *Infection*, 13 (Suppl. 2):224-229 (1985).

Stoll et al., "Monoclonal Antibodies to *Pseudomonas aeruginosa* Lipopolysaccharide and Toxin A," *Clinical Res.* 33(2):420A (Abstract only) (Apr. 8, 1985).

Sawada et al., "Protection Against Infection with *Pseudomonas aeruginosa* by Passive Transfer of Monoclonal Antibodies to Lipopolysaccharides and Outer Membrane Proteins," *J. Infect. Dis.* 150:570-576 (1984).

Olsson et al., "Human-human Hybridomas Producing Monoclonal Antibodies of Predefined Antigenic Specificity," i P.N.A.S., 77:5429-31, (1980).

Poxton, I. R. et al, "The Association on SOS-Polyacrylamide Gels of Lipopolysaccharide and Outer Membrane Proteins of *Pseudomonas aeruginosa* as Revealed by Monoclonal Antibodies and Western Blotting," FEMS Microbiology Letters 27:247-251 (1985).

Sudo et al. Chem. Abst. Vol. 104 (1986) page 147,025m
Fukuda et al. Chem. Abst. Vol. 104 (1986) page 147,026n
Mutharia et al. Chem. Abst. Vol. 100 (1984) page 33,069n
Sawada et al. Chem. Abst. Vol. 101 (1984) page 228,262b

MONOCLONAL ANTIBODY REACTIVE WITH *PSEUDOMONAS AERUGINOSA*

BACKGROUND OF THE INVENTION

The present invention relates generally to hybridoma cell lines and, more specifically, to a hybridoma cell line producing monoclonal antibodies to an antigen common to all strains of *Pseudomonas aeruginosa*.

Today, one of the most important pathogens causing infections in hospitalized patients is *Pseudomonas aeruginosa*. While two decades ago most sepsis contacted in the hospital was attributable to the more acute pathogens such as Staphylococcus and Streptococcus, recently the incidence of the more persistent infection due to gram-negative bacteria, such as *P. aeruginosa*, has increased. This bacterium now accounts for some 200,000 hospital-acquired infections yearly in the United States, about one-third of which are fatal. Symptoms characteristic of bacterial infections of *P. aeruginosa* origin include fever, chills pulmonary complications and septic shock.

Pseudomonas infections are particularly common among patients receiving anti-cancer chemotherapy, cytotix corticosteroids, and immunosuppressive treatment. Infections in such compromised hosts characteristically exhibit resistance to many antibiotics, or develop resistance over the long course of the infection, making conventional treatment difficult. The increasing use of cytotoxic and immunosuppressive therapy combined with selection for drug resistance evoked by the extensive use of antibiotics have contributed to *P. aeruginosa* becoming a pathogen of major clinical significance. Other pseudomonads, such as *P. maltophilia*, are only infrequently associated with serious human infection.

Until recently, determining the pathogen responsible for a bacterial infection, and more particularly, distinguishing *P. aeruginosa* from other gram-negative bacteria, has been difficult and sometimes inconclusive as positive identification could be determined only by culturing the organism in nutrient media in order to expose the characteristic morphology and biochemistry of the colonies. Within the species, however, there are a number of separate strains whose identity can be only laboriously determined. Several taxonomic systems are currently in use for describing these strains or serotypes, including the "International Typing System" which recognizes 17 strains and the more popular Fisher system which recognizes seven serotypes.

All gram-negative bacteria have a lipopolysaccharide moiety (LPS) in the cell wall termed an endotoxin, which is thought to account in major part for the deleterious effects of infections from these microorganisms. The endotoxin is composed of at least three major components: lipid A, core oligosaccharide, and O-specific polysaccharide (the last also termed the O-specific side chains). Each of the strains recognized by the International Typing System exhibits marked chemical differences in the O-specific side chains. Recently, mutant strains of *P. aeruginosa*, such as PAC 605, have been isolated which do not express any O-specific side chains (Meadow et al., J. of General Microbiology 130:631 (1984)).

Because antibiotic treatment remains largely suboptimal against *P. aeruginosa* bacterial infection, attention has increasingly focused on immunologic methods to prevent and control such infections. Immunotherapy involves the administration of antibodies to bolster the native host's defenses against the toxic effects of the bacteria, for example, by enhancing opsonization and phagocytosis of the infecting bacterial cells, or by neutralization of the biological effect of free LPS.

Antibodies directed against antigenic determinants on the O-specific side chains have limited utility for use in immunotherapy because they are effective against only those strains having a complementary or cross-reactive antigenic determinant. The use of such antibodies is thus hampered by their strain specificity. While the core oligosaccharide and lipid A of all strains are thought to share immunological determinants, the few previous attempts to produce and utilize monoclonal antibodies reactive to these regions in Pseudomonas have been largely unsuccessful.

There thus exists a longstanding need for a means of producing antibodies which are reactive with an immunologic determinant common to all strains of *P. aeruginosa* to permit effective diagnosis, prophylaxis and control of bacterial infections attributable to the species. The present invention satisfies these long felt needs and provides related advantages as well.

SUMMARY OF THE INVENTION

The present invention provides a novel hybridoma, identified by deposit #ATCCHB 8909, which is capable of producing monoclonal antibodies which selectively react with antigenic determinants of the lipopolysaccharide which are common to all strains of *Pseudomonas aeruginosa* and to *Pseudomonas maltophilia*, and are not reactive substantially with any antigenic determinant of other clinically important gram-negative bacteria, including other Pseudomonads. The hybridoma is produced by fusing a cell having the ability to replicate indefinitely in cell culture and an immune cell previously immunized with a preparation of a strain of *P. aeruginosa* which does not express the O-side chains. While only a single hybridoma producing a monoclonal antibody against *P. aeruginosa* is described, the present invention is contemplated to encompass all functionally equivalent hybridomas producing monoclonal antibodies which have the functional specificity described herein.

The monoclonal antibodies produced by the hybridoma cell line have use in the detection, prophylaxis and therapy of *P. aeruginosa* and the bacterial infections it causes. In one aspect of the invention, the monoclonal antibodies are used for in vitro immunoassays to detect the presence of *P. aeruginosa* and *P. maltophilia* in preparations and solutions obtained from body fluids and tissues, or from inanimate sources. In another aspect of the invention, the monoclonal antibodies are useful as in vivo imaging agents for detecting areas of localized, pseudomonad infections. Moreover, these monoclonal antibodies are administered prophylactically or therapeutically in order to enhance an organism's ability to neutralize the biological effects of the bacteria, thereby lowering the risk of sepsis. Further, these monoclonal antibodies are used in treatment of existing sepsis and septic shock in patients infected with *P. aeruginosa*. In both prophylaxis and therapy, the monoclonal antibodies enhance the host's own defenses, for example by neutralization of the free LPS and facilitation of opsonization and phagocytosis of the bacterial cells. While *P. maltophilia* does not present a substantial medical problem, it is nevertheless also detectable and treatable by these methods.

Other features and advantages of the present invention will become apparent from the following detailed description which illustrates, by way of example, the principles of the invention.

DESCRIPTION OF THE PREFERRED EMBODIMENTS

The hybridoma cell line prepared by the procedures described herein is exemplified by culture now on deposit with the American Type Culture Collection, 12301 Parklawn Drive, Rockville, MD 20852, U.S.A., which was deposited on Sept. 27, 1985, and is identified by ATCC #HB 8909. Also on deposit is the cell line herein identified as PAC 605 which was deposited on Sept. 27, 1985, and is identified by ATCC #53273.

The present invention involves certain hybrid cells, and their functional equivalents, capable of synthesizing and secreting monoclonal antibodies which selectively react with the lipopolysaccharide (LPS) of P. aeruginosa and P. maltophilia and are not reactive substantially with other clinically important strains of gram-negative bacteria. The invention further involves methods of using these monoclonal antibodies to detect the presence of P. aeruginosa and P. maltophilia and of infections resulting therefrom, and to prophylactically protect against and therapeutically treat P. aeruginosa bacterial infection.

Hybridoma formation and monoclonal antibody production may be effected by many different techniques which are well-known in the art. Basically, the process involves first obtaining immune cells, such as those from spleen of a mammal, which have been previously sensitized with an antigen either in vivo or in vitro. These cells are then fused to cells such as myeloma cells or transformed cells which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro so as to produce large quantities of antibody (for description of the theoretical basis and practical methodology of fusing such cells, see Kohler and Milstein, Nature 256:495 (1975)). While such methods are described in further detail hereinafter, it will be appreciated by those skilled in the art that modifications and additions to the techniques may be made without departing from the scope of the present invention.

Mammalian lymphocytes are immunized by in vivo immunization of the animal or in vitro contact with whole cells or cell extracts of strains of P. aeruginosa which do not exhibit the O-antigen, such as P. aeruginosa strain PAC 605 (obtained from Pauline Meadow, University College, London). This strain, identified by ATCC #53273, is a rough mutant of P. aeruginosa PAC 1R which lacks the O-antigenic side chains of the LPS. Such immunizations are repeated as necessary at intervals of up to a few weeks so as to obtain sufficient titer of antibodies. The cells or cell extracts are carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques (e.g., Milstein and Kohler, Eur. J. Immunol. 6:511 (1976)), for example by using polyethylene glycol (PEG) or other fusing agent. This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described. Enzyme deficiencies may include, for example, thymidine kinase (TK) or hypoxanthine-guanine phosphoribosyl transferase (HGPRT). These deficiencies allow selection for fused cells according to their ability to grow on, for example, hypoxanthine-aminopterin-thymidine medium (HAT). Preferably, the fusion partners utilized are derived from a line which does not secrete immunoglobulin.

Individual fused cells are grown in individual tissue culture wells. Feeder cells, such as irradiated thymocytes or other cells, may be used to increase the viability of the cells. Hybridoma culture supernatants from the individual wells are assayed for antibody binding to P. aeruginosa PAC 605 purified LPS, which does not contain O-specific side chains, or by other suitable detection methods known in the art, such as enzyme-linked immunosorbent assay (EIA) and immunodot assay. For the former, culture supernatants are placed in reaction wells which had been coated with PAC 605 LPS. After incubation, the reaction wells are washed, and remaining antibody bound to the antigen is detected through a labelled antibody reactive with the anti-LPS antibody. Appropriate labels include radioisotopes, luminescent substrates and components of enzymatic reactions.

The Immunodot method is also utilized to screen for clones expressing anti-LPS antibodies (Towbin et al., Immunol. Method 72:313 (1984)). Purified PAC 605 LPS is applied to cellulose nitrate membrane as "dots" and allowed to dry. After blocking in a gelatin solution, the membranes are sequentially immersed in culture supernatant, an anti-mouse IgG peroxidase conjugate solution and a 4-chloro-1-naphthal solution, with phosphate-buffered saline washes in between. Clones expressing reactive immunoglobulin appear as colored dots. Other screening systems known to those in the art may be utilized.

Large quantities of monoclonal antibodies from secreting hybridomas are produced by injecting the clones into the peritoneal cavity of mice and harvesting the ascites fluid therefrom. The mice, preferably primed with pristane or other tumor-promoter and immunosuppressed chemically or by irradiation, may be of various strains, such as New Zealand Black or Balb/c strains. The ascites fluid is harvested from the mice and the monoclonal antibody purified therefrom, for example, by Protein-A Sepharose column or other chromatographic means. High titers of antibodies may be so recovered. Alternatively, the hybridomas may be cultured in vitro and monoclonal antibodies recovered from the culture medium or supernatant.

The monoclonal antibodies so produced have a number of diagnostic and therapeutic uses. In accordance with one aspect of the invention, they are used as in vitro diagnostic agents to test for the presence of *Pseudomonas aeruginosa* in mammals by subjecting body fluids of tissues or other human-derived substances or fluids to standard immunoassay protocols. Additionally, extracts of inanimate objects of which contamination by *P. aeruginosa* would be detrimental, such as medical devices, foodstuffs or water, may also be tested. Such assays may be of a radioimmunoassay, EIA or chemiluminescent format. In one such assay, body fluid is contacted to anti-PAC 605 antibodies and a labelled second antibody used to detect the presence of bacteria to which the anti-PAC 605 antibodies are bound. Alternatively, a competitive immunoassay or a "sandwich" type assay can be employed. Such histochemical methods re well-known in the art; protocols are found, for example, in *Methods in Immunodiagnosis*, 2nd edition, Rose and Bigazzi, eds., John Wiley and Sons, 1980, which is incorporated by reference, and in Campbell et al., *Methods of Immunology*, W. A. Benjamin, Inc., 1964.

Further, monoclonal anti-PAC 605 antibodies are used for the in vivo detection of localized areas of Pseudomonas infection, for example, abscesses or cysts in the soft tissue and osteomyelitis in bone. For such determination, labelled anti-PAC 605 is administered to a mammal suspected of having a *Pseudomonas aeruginosa* (*P. maltophilia*) bacterial infection. The antibody will selectively bind to these bacteria if present in the mammal, thereby concentrating the label in the area of infection. Labels appropriate for such use include radioisotopes, such as $^{125}$Iodine, $^{131}$Iodine, $^{99}$Technetium and $^{111}$Indium, which can then be detected using standard X-ray techniques. Alternatively, the monoclonal antibodies can be labelled with paramagnetic contrast agents, and detected by nuclear magnetic resonance methods. The labelled antibodies thus produce a detectable image of the bacterial abscess.

Monoclonal anti-PAC 605, antibodies are used prophylactically in patients at risk for *P. aeruginosa* infection. Administration of effective amounts of these monoclonal antibodies serves to enhance the body's potential ability to defend against the particular organism, thereby lessening the risk of subsequent infection.

In accordance with a further aspect of the invention, the monoclonal antibodies may be used therapeutically to treat potentially lethal *P. aeruginosa* bacterial infections and septic shock. The antibodies are administered either intravenously or intramuscularly in a physiologically acceptable solution, either alone or in combination with antibiotics. Because the monoclonal antibodies have special affinity for *P. aeruginosa*, they provide selective treatment for such infections, which are otherwise often unresponsive to antibiotic treatment. Among the effects of treatment with these monoclonal antibodies are the facilitation of opsonization and phagocytosis of *P. aeruginosa* cells, presumably by binding to the bacterial cell wall. The monoclonal antibodies thus aid in combating the toxic effects of the bacterial infections.

For all such diagnostic, prophylactic and therapeutic uses, the monoclonal antibodies and other necessary reagents and appropriate devices and accessories may be provided in kit form so as to be readily available and easily used.

The invention will now be described with reference to certain specific examples which are included for the purpose of illustration only and are not intended to limit the invention.

EXAMPLE I

PRODUCTION OF HYBRIDOMAS

Hybridoma techniques: New Zealand Black mice (Jackson Laboratories, Bar Harbor, ME) were immunized with $1 \times 10^8$ formalin-killed cells of *Pseudomonas aeruginosa* strain PAC 605 in Complete Freund's Adjuvant (Difco Laboratories, Detroit, Mich.). The LPS of PAC 605, a bacteriophage-resistant mutant of strain PAC 1R, lacks outer O-specific side chains and consists only of the core LPS (lipid A and core oligosaccharide), as shown by sodium dodecyl-sulfate-polyacrylamide gel electrophoresis (SDS-PAGE) analysis (Meadow et al., J. of General Microbiology 130:631–644 (1984)). After primary immunization, the mice were boosted with an intraperitoneal injection of $1 \times 10^8$ formalin-killed *P. aeruginosa* cells lacking O-specific side chains at one month intervals, PAC 605 for two months.

Four days following the last antigen boost, spleen cells from an immunized mouse were aseptically removed. Following procedures as outlined elsewhere (St. Groth, J. Immuno. Meth. 35:1 (1980)), $5 \times 10^7$ spleen cells were fused with an equal number of SP2/O-AG14, a nonsecreting mouse myeloma cell line of Balb/c origin (obtained from Xoma Corporation, Berkeley, Calif.), using polyethylene glycol 4000 (American Type Culture Collection, Rockville, MD). Hybrid cells were placed into 96-well culture plates (Costar, Cambridge, Mass., #3596) on medium which had been pre-incubated with a feeder layer of normal New Zealand Black thymocytes ($1 \times 10^5$ cells per well, one day before fusion). Cells were cultured at 37° C., in a 10% $CO_2$ atmosphere, in the following medium for the first two weeks: Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1 mM) Gibco, Santa Clara, Calif., #320-1360), penicillin (50 µ/ml)--Streptomycin (50 µ/ml) (Gibco, Santa Clara, Calif., #600-5070), and hypoxanthine-aminopterin-thymidine (HAT) which was prepared by using 1.0% v/v (100X) hypoxanthine-thymidine supplement (Microbiological Associates, Walkersville, Md., #17-782A) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to *P. aeruginosa* purified LPS by EIA (as detailed in Example II) and immunodot assay (as detailed in Example VII). Cultures that were positive on repeated testing were then cloned by limiting dilution techniques. Briefly, the cells were cultured at an estimated 0.1 cells per well in 96-well tissue culture plates (Costar, Cambridge, Mass., #3596). Wells that contained only one colony were identified by microscopic examination, then tested for anti-PAC 605 activity by EIA. Positive clones were expanded onto 24-well tissue cultures plates (Costar, Cambridge, Mass., #3524), re-cloned and retested by the same methods. A single clone, designated XMMPS-605, was found to stably secrete monoclonal antibody; the monoclonal antibody was determined to be of immunoglobulin class IgG$_2$ B by radial immunodiffusion and radioimmunoassay, using standard methods. Other functionally equivalent hybridomas producing functionally equivalent antibodies reactive with *P. aeruginosa* are similarly derived.

New Zealand Black mice (Jackson Laboratories, Bar Harbor, Me.) were used to culture the hybridomas interperitoneally. Approximately $3 \times 10^6$ hybridoma cells were injected intraperitoneally (i.p.) into mice that had been pre-treated as follows: (1) injected i.p. one week earlier with 0.5 ml of pristane (Aldrich Chemical Co., Milwaukee, Wis.), and (2) injected i.p. one day earlier with 2 mg of cyclophosphamide (Adria Laboratories, Columbus, Ohio). The resultant ascites fluid, collected 11-15 days after injection of the hybridomas, contained on average 5 mg/ml of the anti-PAC 605 antibody, XMMPS-605 as determined by radial-immunodiffusion (Meloy, Radial Immunodiffusion, Springfield, Va., Plate #J-307), performed according to the method given in Meloy instruction sheet entitled "Quantitative Immunodiffusion Plates for Mouse Immunoglobulins," which is incorporated by reference.

The antibody in ascites fluid was purified by using a protein-A Sepharose Cl-4B column (Pharmacia, Inc., Piscataway, N.J.) by methods well-known to those skilled in the art, as described elsewhere (Ey, Immunochemistry 15:429-436 (1978)). Determination of immunoglobulin subclass was accomplished by immunodot assay, using sub-class specific antibody conjugated to peroxidase (Southern Biotechnology Associates, Inc., Birmingham, Ala.).

EXAMPLE II

ENZYME-LINKED IMMUNOASSAY (EIA) USING WHOLE BACTERIA

Fifty gram-negative and gram-positive bacteria strains were tested to determine the extent of cross-reactivity of XMMPS-605 monoclonal antibody. The sources of these strains were as follows: (1) *Salmonella minnesota* R595, chemotype Re, strain KNV, was acquired from Dr. Otto Westphal (Max Planck Institute fur Immunobiologie, Freiburg, Federal Republic of West Germany); (2) the international types of *Pseudomonas aeruginosa*, *E. coli* serotypes 055:55 and 026:B6 were purchased from the American Type Culture Collection (ATCC); (3) *P. aeruginosa* PAC 1R, PAC 557, PAC 605, from Pauline Meadow, (University College at London); (4) *P. aeruginosa* Fisher types 1-7 were donated from Dr. Matthew Pollack (Uniformed Services University, Bethesda, Md.); (5) *E. coli* 014:K7 was obtained from Dr. Erwin Neter and Dr. H. Y. Whang (Children's Hospital of Buffalo New York); (6) *E. coli* 085;H9 was obtained from the Center for Disease Control (Atlanta, Ga.); (7) the *Escherichia coli* J5 rough mutant was obtained from Dr. Abraham Braude (University of California, San Diego); (8) the remaining strains were clinical isolates #7711, #3632, #4194 from the UCLA Medical Center.

These bacteria were first cultured on trypticase-soy agar (TSA) plates. Bacterial cells were harvested and their concentration adjusted to $1.5 \times 10^8$ cells/ml in normal saline. Concentrations were determined by the measured absorbance (optical density) of the bacterial suspensions at 570 nanometers (nm). Fifty $\mu$l aliquots of these suspensions were coated onto wells of flat-bottom polyvinyl plates (Falcon LabWare, Oxnard, Calif., #3912), then centrifuged for 30 minutes at $2000 \times G$. Supernatants were discarded and cells were fixed by the addition of 150 $\mu$l/well of 0.25% gluteraldehyde/phosphate buffered saline 0.01M, pH 7.4 (hereinafter PBS) for 15 minutes at room temperature. After washing with PBS, the plates were blocked overnight at room temperature with 0.1% gelatin/PBS.

The remainder of the assay was identical to that described for EIA using LPS (Example III). The plates were washed and 100 $\mu$l/well of affinity-purified XMMPS-605 monoclonal antibody (1 $\mu$g/ml) was allowed to react with the coated antigens for one hour at room temperature. Following a PBS wash, 100 $\mu$l/well of goat anti-mouse IgG peroxidase conjugate was added and allowed to react for one hour at room temperature. After a final wash, 2-2'azino-di(3-athyl-benzthiazolin-sulfonate)(6) (ABTS) (Boehringer Mannheim Biochemicals, Indianapolis, Ind.), substrate was added (100 $\mu$l/well); color development proceeded for 15 minutes, at which point the absorbence at 405 nm was recorded.

The results of these assays are presented in Table 1. All strains of *Pseudomonas aeruginosa* and *P. maltophilia* exhibited significant absorbence at 405 nm (range 0.37 to 1.60 O.D.). Of the other strains of gram-negative bacteria tested, none showed significant reactivity. The antigenic determinant of the lipopolysaccharide with which the monoclonal antibody is reactive is therefore shown to be common to all strains of *P. aeruginosa* and to *P. maltophilia*, but is not present on other gram-negative and gram-positive bacteria.

TABLE 1

| ENZYME-LINKED IMMUNOSORBENT ASSAY (EIA) OF XMMPS-605 BINDING TO WHOLE BACTERIA | |
|---|---|
| BACTERIA | ABSORBENCE AT 405 NM |
| *Pseudomonas aeruginosa* PAC 1R | 0.75 O.D. |
| *Pseudomonas aeruginosa* PAC 557 | 1.60 O.D. |
| *Pseudomonas aeruginosa* PAC 605 | 1.60 O.D. |
| *Pseudomonas aeruginosa* Fisher Type 1 | 0.73 O.D. |
| *Pseudomonas aeruginosa* Fisher Type 2 | 0.76 O.D. |
| *Pseudomonas aeruginosa* Fisher Type 3 | 0.75 O.D. |
| *Pseudomonas aeruginosa* Fisher Type 4 | 1.52 O.D. |
| *Pseudomonas aeruginosa* Fisher Type 5 | 1.53 O.D. |
| *Pseudomonas aeruginosa* Fisher Type 6 | 0.41 O.D. |
| *Pseudomonas aeruginosa* Fisher Type 7 | 0.37 O.D. |
| *Pseudomonas aeruginosa* Internat'l Type 3 | 1.57 O.D. |
| *Pseudomonas aeruginosa* Internat'l Type 4 | 1.55 O.D. |
| *Pseudomonas aeruginosa* Internat'l Type 9 | 1.53 O.D. |
| *Pseudomonas aeruginosa* Internat'l Type 11 | 1.47 O.D. |
| *Pseudomonas aeruginosa* Internat'l Type 12 | 1.54 O.D. |
| *Pseudomonas aeruginosa* Internat'l Type 13 | 1.60 O.D. |
| *Pseudomonas aeruginosa* Internat'l Type 14 | 1.58 O.D. |
| *Pseudomonas aeruginosa* Internat'l Type 15 | 1.57 O.D. |
| *Pseudomonas cepacia* | 0.03 O.D. |
| *Pseudomonas pickettii* | 0.03 O.D. |
| *Pseudomonas putida* | 0.03 O.D. |
| *Pseudomonas maltophilia* | 1.34 O.D. |
| *Salmonella minnesota* R595 | 0.02 O.D. |
| *Escherichia coli* J5 | 0.02 O.D. |
| *Escherichia coli* 014:K7 | 0.01 O.D. |
| *Escherichia coli* 014:H31 | 0.02 O.D. |
| *Escherichia coli* 085:H9 | 0.00 O.D. |
| *Enterobacter cloaceae* | 0.02 O.D. |
| *Serratia Marcescens* | 0.00 O.D. |
| *Klebsiella pneumoniae* | 0.01 O.D. |

EXAMPLE III

ENZYME-LINKED IMMUNOSORBENT ASSAY (EIA) USING PURIFIED LIPOPOLYSACCHARIDE (LPS)

A total of 24 different purified lipopolysaccharide extracts from the bacteria listed on Table 2, were used to determine the extent of cross-reactivity of the anti-PAC 605 monoclonal antibody, XMMPS-605. The LPS of *P. aeruginosa* PAC 605 and that of *Acinetobacter cal-* coaceticus (UCLA clinical isolate #7471) were extracted from the bacterial outer membranes according to published methods (Darveau et al., Jour. of Bacteriology 155:831 (1983) which is incorporated by reference). Purified LPS from *P. aeruginosa* Fisher types 1-7 were obtained from Parke-Davis & Co. (Detroit, Mich.), and the remaining purified antigens were purchased from List Biologicals (Campbell, Calif.).

Preparations of these purified antigens were diluted to 25 µg/ml in water containing 0.5% triethylamine. One hundred µl/well of these antigens were coated onto 96-well EIA plates (Costar, Cambridge, Mass., #3590). Following overnight incubation at room temperature, the plates were blocked with 0.1% reagent grade gelatin (Difco, Inc., Detroit, Mich.) in PBS for two hours at 37° C. This step was essential to prevent nonspecific binding of the antibody to the polystyrene wells. The plates were then washed once with PBS.

Monoclonal antibody XMMPS-605 which had been affinity purified as indicated in Example I, was diluted to 5 µg/ml in 0.1% gelatin/PBS and allowed to react with the coated antigen for one hour at room temperature. After three washings with PBS, 100 µl of the second antibody (peroxidase conjugated goat anti-mouse IgG (Cappel, Malvern, Pa., #0600-3161) was added to the reaction wells, and left to react at room temperature for one hour. The plates were again washed three times with PBS. Positive reactions were detected by adding ABTS (Boehringer Mannheim Biochemicals, Indianapolis, Ind.). This substrate was prepared by first making a stock solution of 20 mg/ml ABTS in 0.1M citrate buffer (pH 4.5). The solution was then diluted 1:50 in citrate buffer and to it was added a 1:1000 dilution of 30% hydrogen peroxide. Color development was allowed to proceed for 15 minutes, and the absorbance was read at 405 nm in a Titertek Elisa Reader (Flow Labs, McLean, Va.). The results of these assays are presented in Table 2, showing the XMMPS-605 antibodies bind only to LPS from *P. aeruginosa* and *P. maltophilia* after testing against LPS from a wide range of gram-negative bacteria. The LPS of all seven of the Fisher strains of *Pseudomonas aeruginosa* and PAC 605 showed absorbence (range 0.78 to 1.06 O.D.). None of the LPS from the remaining gram-negative bacteria tested showed significant absorbence.

Results of these assays are presented in Table 2. As can be seen therein, XMMPS-605 binds to all *P. aeruginosa* representing all Fisher groupings, as indicated by the relatively high levels of absorbence. None of the LPS from other species tested, including preparations of purified core region LPS, exhibited significant absorptance.

TABLE 2

XMMPS-605 BINDING ACTIVITY TO LIPOPOLYSACCHARIDE (LPS) AS DETERMINED BY ENZYME-LINKED IMMUNOABSORBENT ASSAY (EIA)

| ANTIGEN | ABSORBENCE AT 405 NM |
|---|---|
| Pseudomonas aeruginosa PAC 605 | 0.78 O.D. |
| Pseudomonas aeruginosa Fisher 1 | 1.01 O.D. |
| Pseudomonas aeruginosa Fisher 2 | 1.05 O.D. |
| Pseudomonas aeruginosa Fisher 3 | 1.06 O.D. |
| Pseudomonas aeruginosa Fisher 4 | 0.95 O.D. |
| Pseudomonas aeruginosa Fisher 5 | 0.86 O.D. |
| Pseudomonas aeruginosa Fisher 6 | 0.86 O.D. |
| Pseudomonas aeruginosa Fisher 7 | 0.95 O.D. |
| Salmonella minnesota Wild Type | 0.02 O.D. |
| Salmonella minnesota R60 (Ra)* | 0.02 O.D. |
| Salmonella minnesota R345 (Rb)* | 0.08 O.D. |

TABLE 2-continued

XMMPS-605 BINDING ACTIVITY TO LIPOPOLYSACCHARIDE (LPS) AS DETERMINED BY ENZYME-LINKED IMMUNOABSORBENT ASSAY (EIA)

| ANTIGEN | ABSORBENCE AT 405 NM |
|---|---|
| Salmonella minnesota R5 (Rc)* | 0.01 O.D. |
| Salmonella minnesota R7 (Rd)* | 0.03 O.D. |
| Salmonella minnesota R595 (Re)* | 0.01 O.D. |
| Escherichia coli J5 (Rc)* | 0.05 O.D. |
| Escherichia coli K235 | 0.00 O.D. |
| Escherichia coli 011:B4 | 0.00 O.D. |
| Escherichia coli 055:B5 | 0.00 O.D. |
| Escherichia coli 026:B6 | 0.00 O.D. |
| Escherichia coli 0127:B8 | 0.00 O.D. |
| Escherichia coli K12 | 0.01 O.D. |
| Klebsiella pneumoniae | 0.04 O.D. |
| Serratia marcescens | 0.01 O.D. |
| Acinetobacter calcoaceticus | 0.00 O.D. |

*LPS used in assay was a preparation of the core region isolated from mutants which do not express O-side chains.

EXAMPLE IV

ENHANCED OPSONOPHAGOCYTOSIS OF BACTERIA IN PRESENCE OF ANTIBODY

All seven Fisher serotypes were tested in vitro to determine their effect on certain aspects of the immune response with which a host would counteract a bacterial infection, such as opsonization and phagocytosis of invading cells. All bacteria were grown overnight on blood agar. After a visual check for purity, the isolates were transferred to Brain Heart Infusion Broth (BBL Microbiology Sysstems, Cockeysville, Md.) and grown for 4 hours at 37° C. with constant shaking. The bacteria were washed twice with Hanks Balanced Salt Solution (HBSS), and then brought to a concentration of $1 \times 10^8$ organisms/ml by comparing the turbidity to an appropriate McFarland standard.

Opsonophagocytosis was measured in a chemiluminescence assay using a Beckman LS-250 liquid scintillation spectrophotometer (Beckman Instruments, Inc., Fullerton, Calif.). Chemiluminescence is the light released by a white cell after it has engulfed a bacteria. The reaction was performed in the dark, using previously dark-adapted polypropylene scintillation vials. The vials contained 0.9 ml of HBSS, 0.1 ml of luminol ($2 \times 10^{-5}$M) and 0.075 ml of diluted human whole blood. The background was equilibrated for about 15 minutes, to reach approximately 15,000 CPM.

Heparinized blood was obtained from healthy donors. To 5 ml of blood, 1 ml of dextran (6%) was added. The erythrocytes were allowed to sediment for 60 minutes. The upper layer, containing the neutrophils, was centrifuged at $1000 \times G$ for 10 minutes. To lyse the remaining erythrocytes, the pellet was exposed to hypotonic saline (0.22%) for 30 seconds. Then, an equal volume of 1.54% saline was added to restore isotonicity. The neutrophils were suspended in HBSS and the final cell suspension adjusted to $2 \times 10^6$ cells/ml.

For each strain tested with XMMPS-605, a graph of counts per minutes (CPM) vs. time elapsed (minutes) was prepared. Numbers shown on Table 3 indicate maximum CPM values for each strain tested. The time at which maximum counts occured varied according to strain, ranging from 30-80 minutes. These data indicate that for all serotypes except Fisher 1, phagocytosis is enhanced by the addition of XMMPS-605 above that obtained in the control sample containing only HBSS and in the samples containing only pooled human serum.

TABLE 3
CHEMILUMINESCENT DETERMINATION OF OPSONOPHAGOCYTOSIS
XMMPS-605 Activity vs. *Pseudomonas aeruginosa*

| BACTERIA | PEAK COUNTS × $10^3$ | | |
|---|---|---|---|
| | HBSS (Control) | PHS | PHS + PCB5 |
| *P. aeruginosa* PAC 605 | 38 | 36 | 135 |
| *P. aeruginosa* Fisher type 1 | 38 | 36 | 36 |
| *P. aeruginosa* Fisher type 2 | 45 | 85 | 170 |
| *P. aeruginosa* Fisher type 3 | 22 | 60 | 98 |
| *P. aeruginosa* Fisher type 4 | 22 | 30 | 120 |
| *P. aeruginosa* Fisher type 5 | 38 | 82 | 120 |
| *P. aeruginosa* Fisher type 6 | 35 | 45 | 110 |
| *P. aeruginosa* Fisher type 7 | 40 | 50 | 135 |

HBSS = Hank's Balanced Salt Solution
PHS = Pooled Human Serum
PCB5 MoAb: Concentration = 2 μg/ml As a confirmatory method of determining levels of cell death due to opsonization and phagocytosis, direct measurements of bacterial mortality were made. A test containing appropriate medium was innoculated with $2 \times 10^6$ polymorphonuclear cells/ml and $1.5 \times 10^7$ bacteria/ml (ratio 1:10). The tubes were incubated at 37° C. in a water bath. At 0, 60, and 120 minutes, dilutions were made in sterilized water and the number of colony forming units (CFU) growing on Trypticase-Soy Agar (TSA) plates were determined by counting microscopically. The results confirmed the opsonic activity of XMMPS-605 as demonstrated in the chemiluminescent assays.

TABLE 4
MEASUREMENT OF OPSOPHAGOCYTOSIS BY CELL MORTALITY DETERMINATION
PCB5 MoAb Activity vs. *Pseudomonas aeruginosa*

| BACTERIA | Colony forming units/ml × $10^{3*}$ | | |
|---|---|---|---|
| | BACTERIA ONLY | PHS | PCB5 + PHS |
| *P. aeruginosa* Fisher type 1 | 78,000 | 6,800 | 6,800 |
| *P. aeruginosa* Fisher type 2 | 74,000 | 6,100 | 480 |
| *P. aeruginosa* Fisher type 3 | 74,000 | 6,400 | 530 |
| *P. aeruginosa* Fisher type 4 | 76,000 | 6,900 | 49 |
| *P. aeruginosa* Fisher type 5 | 78,000 | 6,400 | 550 |
| *P. aeruginosa* Fisher type 6 | 76,000 | 6,300 | 46 |
| *P. aeruginosa* Fisher type 7 | 75,000 | 590 | 49 |

*Counts of bacteria performed on tubes which were incubated for 60 minutes in a 37° C. water bath.
PHS = Pooled Human Serum
XMMPS-605: Concentration = 2 μg/ml

EXAMPLE V
USE OF XMMPS-605 MONOCLONAL ANTIBODY FOR PROPHYLAXIS

150 μg of affinity purified XMMPS-605 monoclonal antibody was injected i.p. into 4-week-old CD-1 female mice (Charles River Breeding Labs, Inc., Wilmington, Mass.). Live bacteria were prepared as follows: strains of *P. aeruginosa* were grown in Brain Heart Infusion broth (BBL Microbiology Systems, Cockeysville, Md.) overnight at 37° C. The bacterial cells were washed twice with sterile saline, then adjusted to approximately $1 \times 10^9$ cells/ml saline, by comparing the optical density of the cell suspension to a standard curve relating absorbence to viable cell numbers. Approximately 18 hours after XMMPS 605 monoclonal antibody was injected, an approximate $LD_{100}$ dose of *Pseudomonas aeruginosa* cells was injected i.p. into experimental mice and control mice (which received the same protocol, but no XMMPS-605 monoclonal antibody). A previous dose-response study determined the $LD_{100}$, which was defined as the lowest dose that would kill 100% of the mice. Survivors were recorded at 48 hours. The results for individuals receiving Fisher 3 and 4 innoculation at a dosage of about $1 \times 10^8$ cells/individual indicate that pre-treatment with XMMPS-605 conferred enhanced ability to survive the bacterial infection.

TABLE 5
ANIMAL STUDIES: PROPHYLACTIC TREATMENT OF *PSEUDOMONAS AERUGINOSA* INFECTION WITH XMMPS-605

| ORGANISM | SURVIVORS | |
|---|---|---|
| | XMMPS-605 Pre-Treatment | No Pre-Treatment |
| *P. aeruginosa* Fisher 1 (Dose = $1 \times 10^8$ bacteria/individual) | 2/19 | 1/19 |
| *P. aeruginosa* Fisher 2 (Dose = $2.5 \times 10^8$ bacteria/individual) | 4/29 | 3/29 |
| *P. aeruginosa* Fisher 3 (Dose = $1 \times 10^8$ bacteria/individual) | 8/27 (30%) | 4/27 (15%) |
| *P. aeruginosa* Fisher 4 (Dose = $1 \times 10^8$ bacteria/individual) | 13/27 (48%) | 2/27 (11%) |

EXAMPLE VI
IMMUNODOT ASSAY BINDING TO PURIFIED LIPOPOLYSACCHARIDE (LPS)

Purified LPS (100 μg/ml, PBS) was applied to cellulose nitrate membrane (0.20 μm, Sartorius, Hayward, Calif., #11307) as 1 μl "dots" and allowed to air dry for several minutes. The membranes were then blocked in 1.0% reagent grade gelatin/PBS for 30 minutes at room temperature. The remainder of the rapid, room temperature assay was accomplished as follows: Immersion of the antigen treated membranes in culture supernatant (containing XMMPS-605 monoclonal antibody) for 30 minutes, followed by a PBS wash: immersion in goat anti-mouse IgG peroxidase conjugate for 30 minutes, followed by a PBS wash; immersion in 4-chloro-1-naphthol (Sigma Chemical Co., St. Louis, Mo.), substrate for color development of purple, positive "dots." Positive reactions usually occur within 5 minutes. Preparation of substrate: 4-chloro-1-napthol was prepared as a 0.3% stock solution (w/v) in methanol, then diluted 1:5 in 0.01M PBS, to which was added a 1:1000 dilution of 30% hydrogen peroxide.

The dots were scored visually for positive reaction, using a scale of 4+ for strong color to 1+ for weak color. As indicated by the data presented in Table 4, LPS from all Fisher serotypes of *P. aeruginosa* gave a positive reaction (2+ or 3+) indicating binding by XMMPS-605 while no samples of LPS from other bacteria presented discernible color, indicating no binding by XMMPS-605.

TABLE 6
IMMUNODOT ASSAY OF XMMPS-605 BINDING TO PURIFIED LIPOPOLYSACCHARIDES

| ANTIGEN | REACTION** |
|---|---|
| *Pseudomonas aeruginosa* PAC 605 | 2+ |
| *Pseudomonas aeruginosa* Fisher 1 | 3+ |
| *Pseudomonas aeruginosa* Fisher 2 | 3+ |
| *Pseudomonas aeruginosa* Fisher 3 | 3+ |
| *Pseudomonas aeruginosa* Fisher 4 | 3+ |
| *Pseudomonas aeruginosa* Fisher 5 | 3+ |
| *Pseudomonas aeruginosa* Fisher 6 | 3+ |
| *Pseudomonas aeruginosa* Fisher 7 | 3+ |
| *Salmonella minnesota* R60 (Ra)* | —(Neg.) |
| *Salmonella minnesota* R345 (Rb)* | — |
| *Salmonella minnesota* R7 (Rd)* | — |
| *Salmonella minnesota* R595 (Re)* | — |
| *Escherichia coli* J5 (Rc)* | — |
| *Escherichia coli* O55:B5 | — |
| *Klebsiella pneumoniae* | — |
| *Acinetobacter calcoaceticus* | — |

**4+ = strong color; —1+ = weak color
*LPS used in assay was a preparation of the core region isolated from mutants which do not express O-side chains.

EXAMPLE VII
ELECTROPHORETIC TRANSFER AND WESTERN IMMUNOBLOTTING

The electrophoretic transfer of separated lysed whole cells and lipopolysaccharide components from SDS-PAGE gels to nitrocellulose sheet (Sartorius membranes) was adapted from the method of Towbin et al. (Proceedings of Nat. Acad. of Sci. of U.S.A. 76:430-4354 (1979)). The gels were placed in the Bio-Rad trans blot electrophoretic transfer cell (Bio-Rad, Richmond, Calif.) containing 25 mM Tris, 19 mM glycine pH 8.3, 20% v/v methanol and 0.2% w/v SDS. The nitrocellulose sheet was placed on gel toward the anode in order to transfer the image from the gel to the sheet. Electrotransfer using electrophoresis constant power supply (Pharmacia, Inc., Piscataway, N.J.) was carried out at 300 mA for 18 hours. After electroblotting, the nitrocellulose was washed in 0.01M phosphate buffered saline (PBS) at room temperature for 1 hour. The nitrocellulose sheet or strips were washed 3 times. Next, the sheet or strip was incubated for 1 hour with anti-PAC 605 monoclonal antibody at a concentration of 20 µg XMMPS-605/ml in 0.01M PBS pH 7.2. The nitrocellulose sheet was washed twice for 10 minutes each and then incubated in a 1:400 goat anti-mouse IgG peroxidase conjugate (Cappel Laboratories, Malvern, Pa.) (fc fragment specific) for 1 hour. The nitrocellulose sheet was again washed 3 times as described above and the bound peroxidase conjugated second antibody was detected by soaking the nitrocellulose in the substrate-color-reagent 4-chloro-1-naphthol and hydrogen peroxide.

The standards used in the SDS-PAGE were: Cytochrome C (12.4 migration KD); Cytochrome C Dimer (24.8 migration KD); Cytochrome C Trimer (37.2 migration KD); Cytochrome C Tetramer (49.6 migration KD); and Cytochrome C HCX (74.4 migration KD). Molecular weights of bound components were determined relative to these standards.

Figure 1:
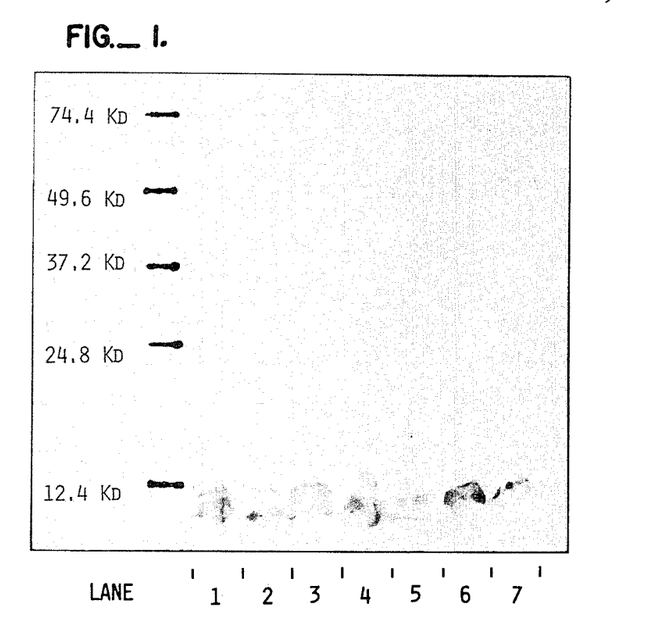
FIG. 1 shows the binding of XMMPS-605 monoclonal antibodies to whole cell lysates of strains of P. aeruginosa.

FIG. 1 shows sodium dodecylsulfate-polyacrylamide gel electrophoresis (SDS-PAGE) analysis of whole cell extracts of *Pseudomonas aeruginosa* binding with XMMPS-605 by Western Immunoblot. The samples are as follows:

| LANE | *P. AERUGINOSA* SEROTYPE |
|---|---|
| 1 | Fisher 1 |
| 2 | Fisher 2 |
| 3 | Fisher 3 |
| 4 | Fisher 4 |
| 5 | Fisher 5 |
| 6 | Fisher 6 |
| 7 | PAC 605 |

For each sample, binding was shown to a low molecular weight component of the cell lysate which migrated to approximately 12 kilodaltons (KD).

Figure 2:
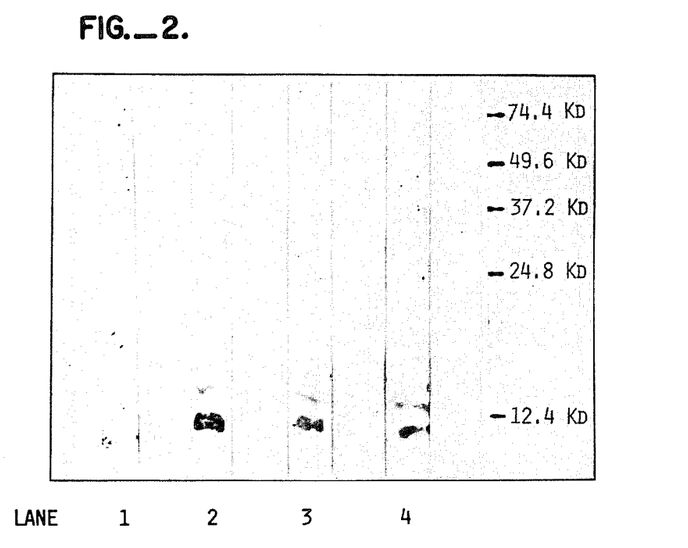
FIG. 2 shows the binding of XMMPS-605 monoclonal antibodies to lipopolysaccharide from various strains of P. aeruginosa.

FIG. 2 shows SDS-PAGE analysis of *P. aeruginosa* lipopolysaccharide binding with XMMPS by Western Immunoblot. The samples are as follows:

| LANE | *P. AERUGINOSA* SEROTYPE |
|---|---|
| 1 | PAC 605 LPS |
| 2 | Fisher 1 LPS |
| 3 | Fisher 2 LPS |
| 4 | Fisher 4 LPS |

FIG. 2 shows a binding pattern similar to that obtained with whole cell lysates, with binding to a low molecular weight component in the region of 12 KD. There is thus shown to be for all Fisher serotypes tested a common LPS component to which XMMPS-605 selectively binds. Lane 7 of FIG. 1 and Lane 1 of FIG. 2 also show binding of XMMPS-605 to a component of PAC 605 which migrates equivalently to a component of the Fisher strains, thus indicating that the antigenic determinant of the 12 KD component is in the core lipopolysaccharide rather than the O-specific side chains as PAC 605 does not express the O-specific side chains.

EXAMPLE VIII
POLYACRYLAMIDE GEL ELECTROPHORESIS (SDS-PAGE) AND SILVER STAINING

Sodium dodecyl sulfate gel electrophoresis was run using a modification of the method of Laemmli (Nature 227:680 (1970)). The slab gels consisted of 10-20% lineal acrylamide gradient with 1.6% bis in 3M Tris-HCl resolving buffer pH 8.8 and 4% acrylamide stacking gel in 0.5M Tris-HCl ph 6.8.

Washed live bacteria ($1 \times 10^{10}$ cells/ml) suspended in saline, purified lipopolysaccharide samples in water (1 mg/ml) were mixed with equal parts of sample buffer containing 0.1 M Tris-HCl, 2% w/v SDS, 10% v/v glycerol, 1% v/v 2-mercaptoethanol and 0.01% bromophenol blue. The mixtures were heated in a 100° C. water bath for 10 minutes and thirty microliters of sample were applied to slab gels. Electrophoresis was run at 35 mA per gel in Tris-glycine buffer pH 8.8 until the tracking dye exited the gels.

The sensitive silver stain method of Tsai and Frasch (Analyt. Biochem. 119:115-119 (1982)) was used to detect lipopolysaccharide in polyacrylamide gels. Electrophoretically resolved denatured whole cell components were stained according to the silver stain method of Morrissey (Anal. of Biochem. 117:307 (1981)).

EXAMPLE IX

THERAPEUTIC TREATMENT OF BACTERIAL INFECTION

Hosts determined to have a bacteremia or other bacterial infection attributable to *Pseudomonas aeruginosa* are treated with monoclonal antibodies reactive with an antigenic determinant common to all strains of the bacterium, such as anti-PAC 605 antibodies, for example, XMMPS-605. The monoclonal antibodies are administered venously, intramuscularly, interperitoneally, or the like, in a physiologically acceptable carrier solution, such as phosphate buffered saline. The dosage is determined by the body weight of the host, it preferably being in the range of about 0.1 mg/kg to about 40 mg/kg body weight, and usually about 1 mg/kg to about 10 mg/kg of host body weight. Alternatively, the dosage is established by evaluating the extent of the remaining infection, as by quantitatively standardized EIA, radioimaging or other methods. Treatment is repeated at intervals as necessary, to effect enhancement of the hosts's ability to recover from the infection.

EXAMPLE X

IMAGING OF LOCALIZED BACTERIAL INFECTION

Monoclonal antibodies which react selectively with an antigenic determinant common to all strains of *Pseudomonas aeruginosa* and to *P. maltophilia*, such as anti-PAC antibodies, for example XMMPS-605, are utilized to determine the location and extent of a localized bacterial infection caused by *P. aeruginosa* by methods well-known in the art, for example, Larson et al., Journal of Clinical Investigation 72:2101 (1983), which is incorporated by reference. Monoclonal antibodies are preferably radiolabelled by radioiodination or by other radio-labelling techniques well-known in the art, such as chelation using a chelating agent such as diethylene-triaminepenta-acetic acid (DTPA); or are otherwise labelled, such as with agents having paramagnetic properties, with chemiluminescent substrates, or with components of an enzymatic reaction. The radio-labelled monoclonal antibodies are purified and formulated for pharmaceutical use. A solution of the labelled monoclonal antibodies in a carrier, for example in phosphate buffered saline, is injected intravenously into a host. The appropriate dose is in the range of about 100 μg to 50 mg. Time is permitted for the antibodies to migrate to regions of the body having concentrations of cells with antigenic determinants reactive therewith. Concentrations of radioisotopes in certain tissues are determined or may be mapped either by techniques of whole body imaging which are well-known in the art, (See, for example, Rainsbury et al., Lancet October 22, 1983, 934 (1983) which is incorporated by reference), or by evaluating biopsied tissue or extracted body fluid using a scintillation counter. Where non-radioactive labels are used, other appropriate monitoring means are employed, such as a detector of nuclear magnetic resonance or a spectrophotometer. Areas of high radiation levels are indicative of the presence of localized infection of *Pseudomonas aeruginosa* or *P. maltophilia*.

EXAMPLE XII

DIAGNOSTIC EIA USING XMMPS-605

Monoclonal antibody XMMPS-605, or its functional equivalent, is utilized in an immunoassay using standard and well-known methods (for example, *Methods in Immunodiagnosis*, 2nd edition, Rose and Bigazzi, eds., John Wiley and Sons, 1980). Such assay may be, for example, of direct format (labelled first antibody reactive with the antigen), an indirect format (a labelled second antibody reactive with the first antibody), a competitive format (for example, addition of labelled antigen), or a sandwich format (both labelled and unlabelled antibody), as well as other formats well-known in the art.

In one such embodiment, a tissue extract from a patient suspected of having a bacterial infection of *Pseudomonas aeruginosa* is applied to an insoluble matrix or solid substrate, such as cellulose strips, agarose or other particles so as to produce a bacteria-substrate complex. Alternatively, the substrate may have attached thereto XMMPS-605 or other antibody reactive with *P. aeruginosa* so as to effect attachment of bacteria from a solution onto the substrate. The substrate is then washed, preferably with PBS, to remove unbound materials.

In a preferred embodiment, the solid substrate with bacteria attached is exposed to a solution having therein XMMPS-605, or other monoclonal antibody specific to *P. aeruginosa* and not reactive with other gram-negative bacteria which might represent the causative agent of the bacterial infection. Such solutions include tissue extracts, serum and urine. The monoclonal antibody is allowed to react with the substrate complex and the complex then washed to remove any unbound monoclonal antibody. The substrate complex is then exposed to a solution having therein a labelled antibody reactive with the monoclonal antibody, such as goat anti-mouse IgG. This antibody is preferably labelled with a radioisotope, such as $^{131}I$, or more preferably with a component of an enzymatic reaction, such as peroxidase, but may also be labelled with a chemiluminescent substrate. The substrate is again washed to remove any unbound antibody. Monitoring means appropriate to the label, such as a scintillation counter or spectrophotometer, are used to determine the presence of label complexed to the substrate, indicative of the presence of *P. aeruginosa* or *P. maltophilia* in the tissue extract.

In addition to use for analyzing solutions of animal origin, similar methods are used to detect the presence of these bacteria on other objects or in other solutions in which *P. aeruginosa* or *P. maltophilia* contamination would be detrimental. Examples of such objects include medical devices for use in invasive procedures, respiratory ventilators, nebulizing humidifiers, oral thermometers, bedside water decanters and even jet fuel.

Although the invention has been described with references to the presently preferred embodiment, it should be understood that various modifications can be made by those skilled in the art without departing from the invention. Accordingly, the invention is limited only by the following claims.

I claim:

1. A hybridoma cell line having the identifying characteristics of ATCC #HB 8909.

2. A monoclonal antibody against Pseudomonas aeruginosa wherein said antibody is produced by the hybridoma cell line having the identifying characteristics of ATCC #HB 8909.

* * * * *